| United States Patent [19] | [11] | 4,202,877 |
|---|---|---|
| Sato et al. | [45] | May 13, 1980 |

[54] ANTIDERMATOMYCOTIC AGENT

[75] Inventors: Masaki Sato, Sagamihara; Takao Kawasaki, Sayama; Yasushi Nagane, Tokyo, all of Japan

[73] Assignee: Kureha Kagaku Kogyo Kabushiki Kaisha, Tokyo, Japan

[21] Appl. No.: 958,973

[22] Filed: Nov. 9, 1978

[30] Foreign Application Priority Data

Nov. 21, 1977 [JP] Japan .................. 52-139717

[51] Int. Cl.² .................. A61K 9/00; A61K 31/11
[52] U.S. Cl. .................. 424/43; 424/333
[58] Field of Search .................. 424/333, 43

[56] References Cited

PUBLICATIONS

Chemical Abstracts, 75:98276r and 8th Coll. Index 7464s (1971).
Chemical Abstracts, 55:12743f (1961).
Chemical Abstracts, 48:11730g (1954).
Chemical Abstracts, 41:2195e (1947).

*Primary Examiner*—Leonard Schenkman
*Attorney, Agent, or Firm*—Stevens, Davis, Miller & Mosher

[57] ABSTRACT

Pharmaceutical compositions and a method for treating dermatophytes are based upon the antidermatophytic activity of o-methoxycinnamaldehyde.

9 Claims, 2 Drawing Figures

ANTIDERMATOMYCOTIC AGENT

DETAILED DESCRIPTION OF THE INVENTION

The present invention relates to an antidermatophytic agent against dermatophytes belonging to the genera Trichophyton, achorion and Endodermophyton, which contains o-methoxycinnamaldehyde as its active ingredient.

A large number of drugs for the therapy of dermatomycosis have been used up to now but have not necessarily been found satisfactory in their therapeutical effect. The therapy of dermatomycosis usually takes a long time and so, in most cases, involves side effects by applied drugs. This is proved by many clinical reports.

For the therapy by internal medicine, there is a known use of an antibiotic, griseofulvin, in large dose. However, a side effect is caused by the antibiotic due to its oral administration, thus it is difficult to achieve its therapeutical effect in a satisfactory way.

For external treatment, on the other hand, there are commercially sold a variety of therpeutical drugs for the dermatomycosis but it has been found that, in spite of their high antimicrobial activity, they do not always show satisfactory clinical results. Especially, most of the chemically synthesized antimicrobial preparations exhibit toxicity to human body.

Accordingly, there is a strong demand for development of an antidermatophytic agent or drug which shows less side effects but high clinical results.

The inventors have therefore made an extensive study of materials of natural origin to derive therefrom an antidermatophytic substance which involves no chemical change and is innoxious to human body and high in antidermatophytic effect and, as a result, it has been found that an extract from cinnamon powder is suitable for the above purpose. The present invention is based on the above finding.

Cinnamon powder useful as a starting material in the practice of the present invention is prepared from a plant Cinnamomum cassia Blume of the family Lauraceae, the plant being widely distributed over Southeastern Asia, southern China and India. Due to its strong aromaticity, cinnamon powder is widely used in the world as an aromatic stomachic or a corrective and, especially in China, it is favorably employed as a diaphoretic, antipyretic or anodyne.

Thus, cinnamon powder not only exhibits a wide range of pharmaceutical activities but also is extremely safe for human body and is advantageously produced in great amount, thus being very favorable as the starting material for such an antidermatophytic agent. Though the cinnamon powder shows such various pharmaceutical activities as mentioned above, it is not clearly understood what component or components thereof serve for the pharmaceutical activities.

It has been now found that a substance which is obtained by repeated purification of an extract from cinnamon powder and shows a therapeutical effect on dermatomycosis is o-methoxycinnamaldehyde. This substance is of the natural origin and shows little or no adverse effect on human body. Cinnamon powder used as the raw material in the present invention may be made from the bark, the velamen, the timber and the leaves of Cinnamomum cassia Blume and these are used after drying and pulverizing.

In order to isolate the above-mentioned active component from cinnamon powder according to the present invention, the finely pulverized cinnamon is advantageously extracted with an organic solvent, followed by concentrating to obtain a crude extract. The thus obtained crude extract is purified in the following manner: The organic solvent used may be any of those ordinarily employed for general extraction procedures.

The crude extract is purified by column-chromatography using an adsorbent such as silica gel, active carbon or the like, or by thin-layer chromatography using the same adsorbent as above or by combination of the above-mentioned procedures and eluted by n-hexane, benzene, chloroform, methanol or the like solvent. Then, the resulting solution is heated to evaporate the solvent therefrom to obtain a syrupy substance. Preferably, the above-mentioned procedure is repeated several times and the finally obtained syrupy substance is recrystallized to give a purified substance.

The substance thus obtained (hereinlater referred to as the present substance) is found to have a melting point of 45° to 46° C. and, a boiling point of 295° C. From the results of elemantary analysis, infrared absorption spectral analysis and determinations such as of the melting point, it is assumed that the present substance is o-methoxycinnamaldehyde of the following formula:

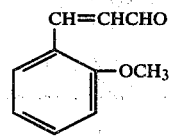

For confirmation, the inventors have synthesized o-methoxycinnamaldehyde by bringing into reaction of o-methoxybenzaldehyde with acetaldehyde, distilling the resulting reaction product under reduced pressure to collect a fraction distilling in a range of from 100° to 130° C./3 mmHg, and purifying the fraction by recrystallization. The thus synthesized o-methoxycinnamaldehyde was analytically compared with the present substance isolated from cinnamon powder by the extraction and purification procedure, revealing that the both substances were identical to each other in the elementary analytical values, the infrared absorption spectra and the melting points and that no depression of melting point was observed when the both substances were subjected to a mixed examination.

From the above results, it was confirmed that the substance which is present in cinnamon and shows a potential antimycotic activity is ortho-methoxycinnamaldehyde as assumed hereinabove.

The present substance, o-methoxycinnamaldehyde, has the following physical and physilogical properties.

(1) Physical properties melting point=45°–46°

Boiling point=

295° C.

160°–161° C./12 mmHg

Solubility=Soluble in methanol, ethanol, acetone, benzene and chloroform but insoluble in water.

(2) Acute toxicity and subacute toxicity

Ortho-methoxycinnamaldehyde was suspended in a mixed sulution of 1 part of Tween (mfd. Atlas Powder Co.) and 2 parts of a physiological salt solution. Commercially available ICR-JCL female mice (with a body weight of 22±1 g) were used for the toxicity tests, in which the mice were divided into groups, one being subjected to the percutaneous administration (p.c.) and the other group subjected to the oral administration (p.o.) and, one week after the administration their mortality was observed. Then, $LD_{50}$ value was determined by the Litchfield-Wilcoxon method, with the results shown in Table 1 below. For comparison, the crude extract was similarly tested to determine its $LD_{50}$ value.

From these results, it has been found that the present substance is safe even when administered in large dose. One week after the oral administration of the present substance, the mice were killed and autopsied, revealing that no specific abnormal finding was obtained in appearance and also in visceral observation. In addition, no specific toxic sympton was observed.

Further, in order to determine the subacute toxicity of the present substance, it was administered to mice every day over 3 months via an oral and a percutaneous routes using the dosage of 100 mg/kg and 250 mg/kg, respectively. As a result, neither death nor abnormal symptom was observed.

Table 1

Acute Toxicity

| Specimen | Route of administration | Number of tested mice | $LD_{50}$(mg/kg) |
|---|---|---|---|
| Crude extract | oral (p.o) | 10 | 12000 |
| o-methoxycinnamaldehyde | oral (p.o) | 10 | 4430 |
| o-methoxycinnamaldehyde | Percutaneous (p.c.) | 10 | 8670 |

ANTIMICROBIAL SPECTRUM

The antimicrobial spectrum was determined using Sabouraud's medium. Three hundred milligrams of o-methoxycinnamaldehyde was dissolved in 15 ml of methanol and diluted to give solutions with different concentrations. An aliquot of 0.1 ml of the solutions was charged into a test tube.

Each 10 ml of the sterilized Sabouraud's medium of pH of 5 to 6 was charged into each of the above-mentioned test tube and well mixed with the solution of the present substance.

A variety of microbial species were provided and each species was suspended in a physiological salt solution in an amount of $10^5$/ml. One tenth milliliter of the mycotic suspension was inoculated to the medium in the above-mentioned test tube and cultivated at 25° C. for 3 days so as to observe the state of growth and also to determine the minimum growth inhibiting concentration (MIC) of the present substance, with test results shown in Table 2 below.

Table 2

| No. | Tested microorganism | Minimum growth inhibiting concentration (MIC) |
|---|---|---|
| 1 | Trichophyton mentagrophytes | 12.5 ppm |
| 2 | Trichophyton rubrum | 12.5 |
| 3 | Microsporum gypseum | 25.0 |
| 4 | Microsporum canis | 6.25 |
| 5 | Aspergillus fumigatus | 100 |
| 6 | Aspergillus niger | 200 |
| 7 | Candida albicans | 50 |
| 8 | Cryptococcus neoformans | 12.5 |
| 9 | Escherichia coli | 60 |
| 10 | Staphylococcus aureus | 50 |

As is seen from the above results, the present substance possesses a wide range of antimicrobial spectrum and is usable an an antimicrobial agent, particularly useful as an antidermatophytic agent.

In addition, the present substance is low in toxicity and is substantially safe to the human body.

CLINICAL RESULTS

A 41-year-old man who had suffered from ring-worm of trichophytia pompholyciformis over 10 years was applied with an ointment of the present substance, which had been prepared by a method as will be described hereinlater, on the affected parts twice a day.

There was produced a remarkable effect from the 4th day after the application and the itchiness was gone. On 15th day after the application, it was found that the appearance of the affected parts has been restored to normal appearance. The application was continued for further 25 days. Even one year after the application, he suffered no relapse.

Separately, a tincture containing 3% of the present substance (its preparation will be described hereinafter) was applied, twice a day, to affected parts of patients of trichophytia interdigitalis, trichophytia pompholyciformis and eczema marginatum. The application was continued for 30 days and the affected parts were investigated. The test results are shown in Table 3. From the results it is be seen that the present substance gives a remarkable curing effect on dermatomycosis of human body.

Table 3

| Symptom | Number of cases | Days of application | Number of Cured cases |
|---|---|---|---|
| trichophitia pompholyciformis | 22 | 30 | 18 |
| eczema marginatum | 20 | 30 | 18 |
| trichophytia interdigitale | 15 | 30 | 14 |

PREPARATIONS

An antidermatophytic agent according to the present invention which contains o-methoxycinnamaldehyde as its active ingredient may be prepared in various forms, i.e. an ointment, aerosol foam, tincture, lotion, solution or the like, by any of techniques known to those skilled in the art and using known excipients. That is, the ointment can be prepared by adding to the present substance a carrier such as an oily ointment base, a hydrophilic ointment or an absorption ointment base, e.g. vaseline (petroleum jelly), propylene glycol, polyethylene glycol or other various bases. The aerosol foam can be formed by dissolving the present substance in a solvent, charging the solution together with a pressurized gas such as carbon dioxide, nitrogen gas or furon 114 into a pressure container, and then spraying the mixture from a nozzle. The tincture can be obtained by dissolving the present substance in an alcohol or propylene glycol.

The lotion may be either a shake lotion or an emulsive lotion.

Preparative examples of these preparations are described hereinafter.

(a) Tincture

| | | |
|---|---|---|
| o-methoxycinnamaldehyde | 3 g | } mixed together |
| 80% ethanol | 4 | |

| | |
|---|---|
| prophylene glycol  1 | } 97 g |

(b) Ointment

Two grams of o-methoxycinnamaldehyde is dissolved under heating conditions in 150 g of propylene glycol, and the solution is then added to 300 g of vaseline of 80° C. with agitation and cooled to obtain an ointment.

(c) Aerosol foam

Two grams of o-methoxycinnamaldehyde is dissolved in 150 g of propylene glycol, and the solution is introduced together with pressurized carbon dioxide gas into a pressure container to give an aerosol by spraying.

(d) Suspension

Three grams of o-methoxycinnamaldehyde is dispersed in 100 ml of a suspending liquid (Tween 80: physiological salt solution = 1:2).

The amount of the agent of the present invention applied to affected part may depend on the symptom and area of the affects part and the agent is applied several times, preferably twice a day. In general, the agent is applied, as o-methoxycinnamaldehyde, in an amount of $10^{-3}$ to $10^3$ mg, preferably $10^{-2}$ to $10^2$ mg, per cm$^2$ of affected part.

As will be understood from the foregoing, the agent according to the present invention is almost completely free of toxicity to human body and shows a wide range of antimicrobial spectrum, so that it is effective for the therapy of dermatomycosis of domestic animals and other mammals, not to mention the antidermatophytic activity with regard to human body. In addition, the agent of the invention is also usable as an antimicrobial agent.

The o-methoxycinnamaldehyde which is an active ingredient of the agent according to the present invention can be provided at low cost since it can be produced simply by synthesis without resorting to a complicated procedure using cinnamon powder and including an extraction from cinnamon powder, isolation and purification. The substance obtained by the synthesis method is identical in physical properties and antimicrobial activity to that obtained from the extraction method. In this sense, the present invention greatly contributes to the therapy of dermatomycosis.

The preparation of o-methoxycinnamaldehyde from cinnamon powder will be described by way of an example.

EXAMPLE

Powdered cinnamon was shaken together with chloroform for 20 minutes for extraction and the resulting extraction solution was concentrated to obtain a crude extract.

The crude extract was poured into a column packed with silica gel (Wako Gel C 200) and the adsorbate was eluded with a mixture of benzene and chloroform (9:1), then with chloroform, and finally with methanol in this order. The fraction eluded with the benzene-chloroform mixture (9:1) was collected.

Figure 1:
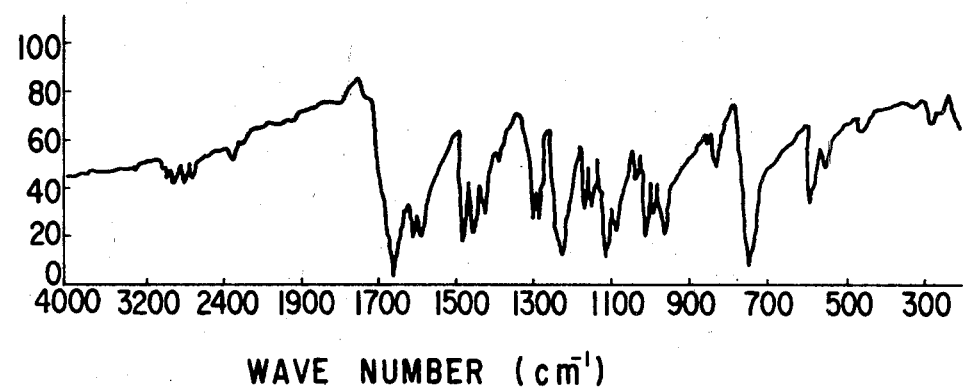
FIG. 1 is an infrared absorption spectrum of o-methoxycinnamaldehyde obtained from naturally occurring cinnamon.

The thus collected fraction was passed for adsorption through a clumn packed with active alumina (Wako Active Alumina 90 with a neutral activity of 1), followed by elution with the above-mentioned solvents in that order to collect a fraction eluded with chloroform. The fraction was developed with benzene using a thin layer of silica gel (product of E. Merck Co., Kiesel gel, thickness of 0.25 mm). A spot-portion emitting a green fluorescence of $R_f=0.4$ was scrapped followed by extracting it with chloroform, and distilling off the chloroform to obtain a syrupy substance light yellow in color. The above procedure was repeated two times and a finally obtained syrup was cooled to crystallize. The resulting crystals were recrystallized from a small amount of methanol to obtain crystals showing a melting point of 45.8° C. and containing, as determined by an elementary analysis, 74.25% of carbon and 6.20% of hydrogen (its constituent elements being carbon, hydrogen and oxygen). The infrared absorption spectrum of the crystals is shown in FIG. 1 of the accompanying drawings.

In order to identify the crystals to be o-methoxycinnamaldehyde, authentic o-methoxycinnamaldehyde was synthesized by the following procedure.

Figure 2:
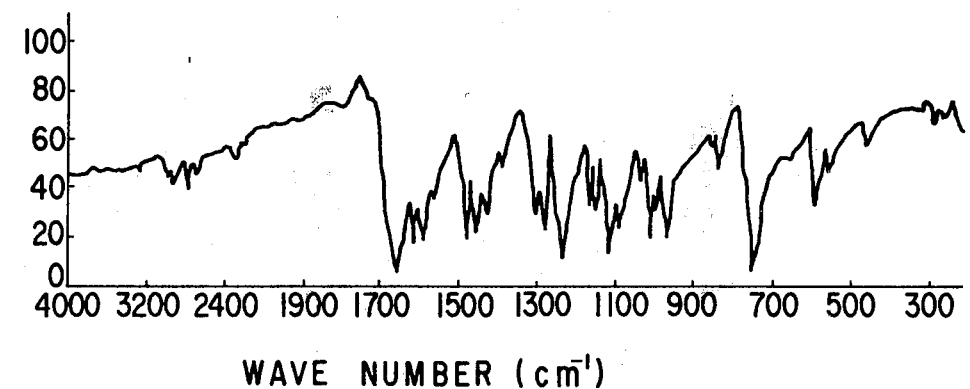
FIG. 2 is an infrared absorption spectrum of o-methoxycinnamaldehyde obtained by a synthetic method.

Ten grams of sodium hydroxide and 50 g of o-methoxybenzaldehyde were dissolved in a mixture of 300 ml of ethanol and 400 ml of water, to which was dropwise added 40 g of acetaldehyde at 0°-5° C. under agitation. After completion of the addition, the agitation was continued for about 2 hours at the same temperature as indicated above, and then 400 ml of water was added to the mixture. The mixture was extracted with benzene. The benzene layer was washed with water and dried, and benzene was distilled off to obtain a reddish brown syrupy substance. The thus obtained surupy substance was subjected to a distillation under reduced pressure to collect a fraction having a boiling point of 100°-300° C./3 mmHg. The fraction was cooled to solidify, and then recrystallized from a small amount of methanol to obtain 36.9 g of colorless crystals. The crystal showed a melting point of 45.5° C. and contained, as determined by an elementary analysis, 74.14% of carbon and 6.19% of hydrogen. The infrared absorption spectrum of the thus obtained o-methoxycinnamaldehyde is shown in FIG. 2.

From the above, it is seen that the synthesized o-methoxycinnamaldehyde has the same melting point, values determined by elementary analysis, and infrared absorption spectrum as the crystals obtained from the cinnamon powder. When the crystals obtained from the cinnamon powder and the synthesized substance were subjected to a mixed examination, no depression of melting point was observed.

What is claimed is:

1. An antidermatophytic composition which comprises an effective amount of o-methoxycinnamaldehyde capable of inhibiting dermatophytes upon topical application to a patient suffering therefrom, together with a topical carrier therefor, said composition being in the form of an ointment, aerosol foam composition, tincture or suspension.

2. An antidermatophytic composition of claim 1, wherein said composition is in the form of an ointment.

3. An antidermatophytic composition of claim 2, wherein said ointment contains petroleum jelly, propylene glycol or polyethylene glycol.

4. An antidermatophytic composition of claim 1, wherein said composition is in the form of an aerosol foam composition.

5. An antidermatophytic composition of claim 4, wherein said aerosol foam composition is a pressurized solution which upon release of said aerosol foam composition from a pressurized container forms the desired foam.

6. An antidermatophytic composition of claim 1, wherein said composition is in the form of a tincture.

7. An antidermatophytic composition of claim 6, wherein said tincture contains an alcohol or propylene glycol.

8. A method of treating a human patient suffering from dermatomycosis which comprises contacting the skin area afflicted by dermatomycosis with an effective amount of o-methoxycinnamaldehyde capable of inhibiting dermatomycosis.

9. The method of claim 8 wherein the o-methoxycinnamaldehyde is applied in an amount of $10^{-3}$ to $10^3$ mg per one $cm^2$ of the affected part.

* * * * *